United States Patent [19]
Oka et al.

[11] Patent Number: 5,729,203
[45] Date of Patent: Mar. 17, 1998

[54] EMERGENCY CALL SYSTEM

[75] Inventors: Tohru Oka, Ichinomiya; Hidenori Suzuki, Nagoya, both of Japan

[73] Assignee: Colin Corporation, Aichi, Japan

[21] Appl. No.: 436,427

[22] PCT Filed: Jun. 28, 1994

[86] PCT No.: PCT/JP94/01036

§ 371 Date: May 24, 1995

§ 102(e) Date: May 24, 1995

[51] Int. Cl.$^6$ .............. G08B 23/00; A61B 5/04
[52] U.S. Cl. .............. 340/573; 340/574; 128/696; 128/903; 128/904
[58] Field of Search .............. 340/573, 574, 340/539, 286.07, 825.03; 128/696, 670, 630, 632, 903, 904, 702; 364/413.02, 413.03, 413.04, 413.05, 413.06

[56] References Cited

U.S. PATENT DOCUMENTS

| | | | |
|---|---|---|---|
| 3,572,316 | 3/1971 | Vogelman et al. | 128/690 |
| 3,902,478 | 9/1975 | Konopasek et al. | 128/690 |
| 3,972,320 | 8/1976 | Kalman | 128/690 |
| 4,173,971 | 11/1979 | Karz | 128/904 |
| 4,524,243 | 6/1985 | Shapiro | 340/573 |
| 4,622,979 | 11/1986 | Katchis et al. | 128/904 |
| 4,819,860 | 4/1989 | Hargrove et al. | 340/573 |
| 4,889,131 | 12/1989 | Salem et al. | 128/903 |
| 5,131,390 | 7/1992 | Sakaguchi et al. | 128/632 |
| 5,131,400 | 7/1992 | Harada et al. | 128/687 |
| 5,162,776 | 11/1992 | Bushnell et al. | 340/573 |
| 5,226,425 | 7/1993 | Righter | 128/904 |
| 5,289,824 | 3/1994 | Mills et al. | 128/904 |
| 5,462,051 | 10/1995 | Oka et al. | 128/630 |
| 5,469,146 | 11/1995 | Gurler | 340/539 |
| 5,515,858 | 5/1996 | Myllymaki | 128/690 |
| 5,581,369 | 12/1996 | Righter et al. | 128/904 |

*Primary Examiner*—Brent A. Swarthout
*Assistant Examiner*—Van T. Trieu
*Attorney, Agent, or Firm*—Oliff & Berridge, PLC

[57] ABSTRACT

A host monitor device 26 disposed in an emergency call center 12 displays, on an image display 82 thereof, an ID code identifying a subscriber 20, a symbol representing an emergency call from the subscriber 20, a symbol indicating that a portable transmitting device 22 is worn, or not worn, on the subscriber 20, and pulse-wave information including the respective times of day, and total number, of occurrences of arrhythmia, tachycardia, or bradycardia of the subscriber 20 detected in a prescribed time duration. An operator 84 can check the emergency call of the subscriber 20 against the pulse-wave information of the same 20 transmitted to the emergency call center 12 when a call button 34 is operated by the subscriber 20. Thus, the operator 84 can immediately judge whether an emergency action should be taken for the subscriber 20, in response to the emergency call of the same 20, without needing an additional checking operation such as a telephone call to the subscriber 20.

15 Claims, 6 Drawing Sheets

EMERGENCY CALL SYSTEM

FIELD OF THE ART

The present invention relates to an emergency call system for transmitting an emergency call of a subscriber to an emergency call center via a communication channel.

BACKGROUND OF THE INVENTION

There is known an emergency call system for transmitting an emergency call of a subscriber to an emergency call center via a communication channel. An example of the emergency call system includes a portable transmitting device of a pendant type which is adapted to be worn on a subscriber and transmits an emergency call signal in response to an operation of a call button by the subscriber, and a signal receiving and call device which receives the radio-wave signal from the portable transmitting device and calls the emergency call center via the communication channel. When the subscriber sends an emergency call to the emergency call center by using the emergency call system as described above, an operator of the emergency call center calls back the subscriber to check that the subscriber is in an abnormal situation, and judges whether an emergency action should be taken for the subscriber. If the operator judges that an emergency treatment should be given to the subscriber, then he or she requests an ambulance car or the like to be sent to the subscriber.

In the conventional emergency call system as described above, the portable transmitting device transmits only an emergency call signal in response to an operation of the call button by a subscriber. Thus, it is very cumbersome for the operator of the emergency call center to check each of a number of emergency calls and judge whether that call really requires an emergency action. Namely, some of the emergency calls resulting from subscriber's operation of the call button of the portable transmitting device are transmitted upon unintentional operation of the call button, transmitted for checking that the call system works properly, or transmitted with just the intention of talking with the operator of the call center.

The present invention has been developed in view of the above-described situation and it is therefore an object of the present invention to provide an emergency call system wherein an operator can easily judge whether an emergency call of a subscriber really requests an emergency action, without needing an additional checking operation.

DISCLOSURE OF THE INVENTION

It is therefore an object of the present invention to provide an emergency call system for transmitting an emergency call of a subscriber to an emergency call center via a communication channel, comprises: (a) a portable transmitting device having a call button which is operable for transmitting the emergency call of the subscriber, a physical information sensor which obtains a physical information of the subscriber, a memory which stores a batch of physical information detected by the physical information sensor for a predetermined time duration, and a signal transmitter which transmits a signal at a predetermined modulation frequency, the portable transmitting device being adapted to be worn on said subscriber, and transmitting from the signal transmitter a signal representing the batch of physical information stored in the memory for the predetermined time duration in response to an operation of the call button; and (b) a signal receiving and call device having a signal receiver which receives the signal transmitted from the signal transmitter of the portable transmitting device, and a communication apparatus which transmits the physical information signal received by the signal receiver to the emergency call center via the communication channel, the signal receiving and call device being disposed in a place where the subscriber is.

In the emergency call system in accordance with the above-described, first aspect of the present invention, the portable transmitting device transmits the signal representing the batch of physical information stored in the memory for the predetermined time duration, in response to the operation of the call button. The signal receiving and call device receives the physical information signal transmitted from the portable transmitting device and transmits the physical information signal to the emergency call center.

In the emergency call center, the emergency call can be checked against the physical information of the subscriber obtained in the predetermined time duration before the operation of the call button. Therefore, it is possible to immediately judge whether the emergency call really requests an emergency action, without needing an additional checking operation such as a telephone call to the subscriber, so that an emergency action such as requesting an ambulance car is immediately taken.

Preferably, the portable transmitting device comprises a wearing sensor which identifies whether the portable transmitting device is worn on the subscriber and outputs a wearing signal indicating that the portable transmitting device is worn on the subscriber. The signal transmitter transmits the wearing signal and the physical information signal in response to the operation of the call button. The signal receiving and call device transmits the wearing signal and the physical information signal transmitted from the signal transmitter, to the emergency call center.

Preferably, the portable transmitting device comprises an abnormality identifying means for identifying whether the subscriber is abnormal, based on the physical information of the subscriber detected by the physical information sensor. The signal transmitter transmits the signal representing the batch of physical information stored in the memory for the predetermined time duration in response to an identification of the abnormality identifying means that the subscriber is abnormal.

Preferably, the physical information sensor comprises at least one of a pulse wave sensor which detects a pressure pulse wave produced from an arterial vessel of the subscriber, an electrocardiogram sensor which obtains an electrocardiogram from the subscriber, a body temperature sensor which measures a body temperature of the subscriber, and a sweat sensor which measures an amount of sweat perspired from the subscriber.

Preferably, the communication channel comprises a telephone line which is connected to a telephone disposed in the place where the subscriber is.

According to a second aspect of the present invention, there is provided an emergency call system for transmitting an emergency call of a subscriber to an emergency call center via a communication channel, comprises: (a) a portable transmitting device having a call button which is operable for transmitting the emergency call of the subscriber, a physical information sensor which obtains a physical information of the subscriber, a memory which stores a batch of physical information detected by the physical information sensor for a predetermined time duration, and a signal transmitter which transmits a signal at a predetermined modulation frequency, the portable transmitting device being adapted to be worn on the subscriber, and transmitting from the signal transmitter a signal representing the batch of physical information stored in the memory for the predetermined time duration in response to an operation of the call button; and (b) a signal receiving and call device having a signal receiver which receives the signal transmitted from the signal transmitter of the portable transmitting device, an analyzing device which analyzes the signal received by the signal receiver, and a communication apparatus which transmits a signal representing an analysis of the analyzing device to the emergency call center via the communication channel, the signal receiving and call device being disposed in a place where the subscriber is.

In the emergency call system in accordance with the second aspect of the present invention, the portable transmitting device transmits the signal representing the batch of physical information stored in the memory for the predetermined time duration, in response to the operation of the call button. The signal receiving and call device receives the physical information signal, which then is analyzed by the analyzing device of the signal receiving and call device so that the analyzed results of the physical information of the subscriber are transmitted to the emergency call center.

In the emergency call center, the emergency call can be checked against the analyzed results of the physical information of the subscriber obtained in the predetermined time duration before the operation of the call button. Therefore, it is possible to immediately judge whether the emergency call really requests an emergency action, without an additional checking operation such as a telephone call to the subscriber, so that an emergency action such as requesting an ambulance car is immediately taken.

Preferably, the portable transmitting device comprises a wearing sensor which identifies whether the portable transmitting device is worn on the subscriber and outputs a wearing signal indicating that the portable transmitting device is worn on the subscriber. The signal transmitter of the portable transmitting device transmits the wearing signal and the physical information signal in response to the operation of the call button. The signal receiving and call device transmits the wearing signal transmitted from the signal transmitter, and the signal representing the analysis of the analyzing device, to the emergency call center.

Preferably, the portable transmitting device comprises an abnormality identifying means for identifying whether the subscriber is abnormal, based on the physical information of the subscriber detected by the physical information sensor. The signal transmitter transmits the signal representing the batch of physical information stored in the memory for the predetermined time duration in response to an identification of the abnormality identifying means that the subscriber is abnormal.

Preferably, the physical information sensor comprises at least one of a pulse wave sensor which detects a pressure pulse wave produced from an arterial vessel of the subscriber, an electrocardiogram sensor which obtains an electrocardiogram from the subscriber, a body temperature sensor which measures a body temperature of the subscriber, and a sweat sensor which measures an amount of sweat perspired from the subscriber.

Preferably, the physical information sensor comprises a pulse wave sensor which detects a pressure pulse wave from the subscriber, wherein the analyzing device analyzes the pressure pulse wave regarding at least one kind of information selected from the group consisting of a pulse rate, a waveform of a pressure pulse wave, a magnitude of a pressure pulse wave, and a blood pressure corresponding to a peak magnitude of a pressure pulse wave.

Preferably, the communication channel comprises a telephone line which is connected to a telephone disposed in the place where the subscriber is.

Preferably, the signal receiving and call device further comprises a display device which displays the analysis of the analyzing device so that the subscriber is informed of the analysis.

BEST MODE FOR CARRYING OUT THE INVENTION

Hereinafter, there will be described an embodiment of the present invention in conjunction with the accompanying drawings.

Figure 1:
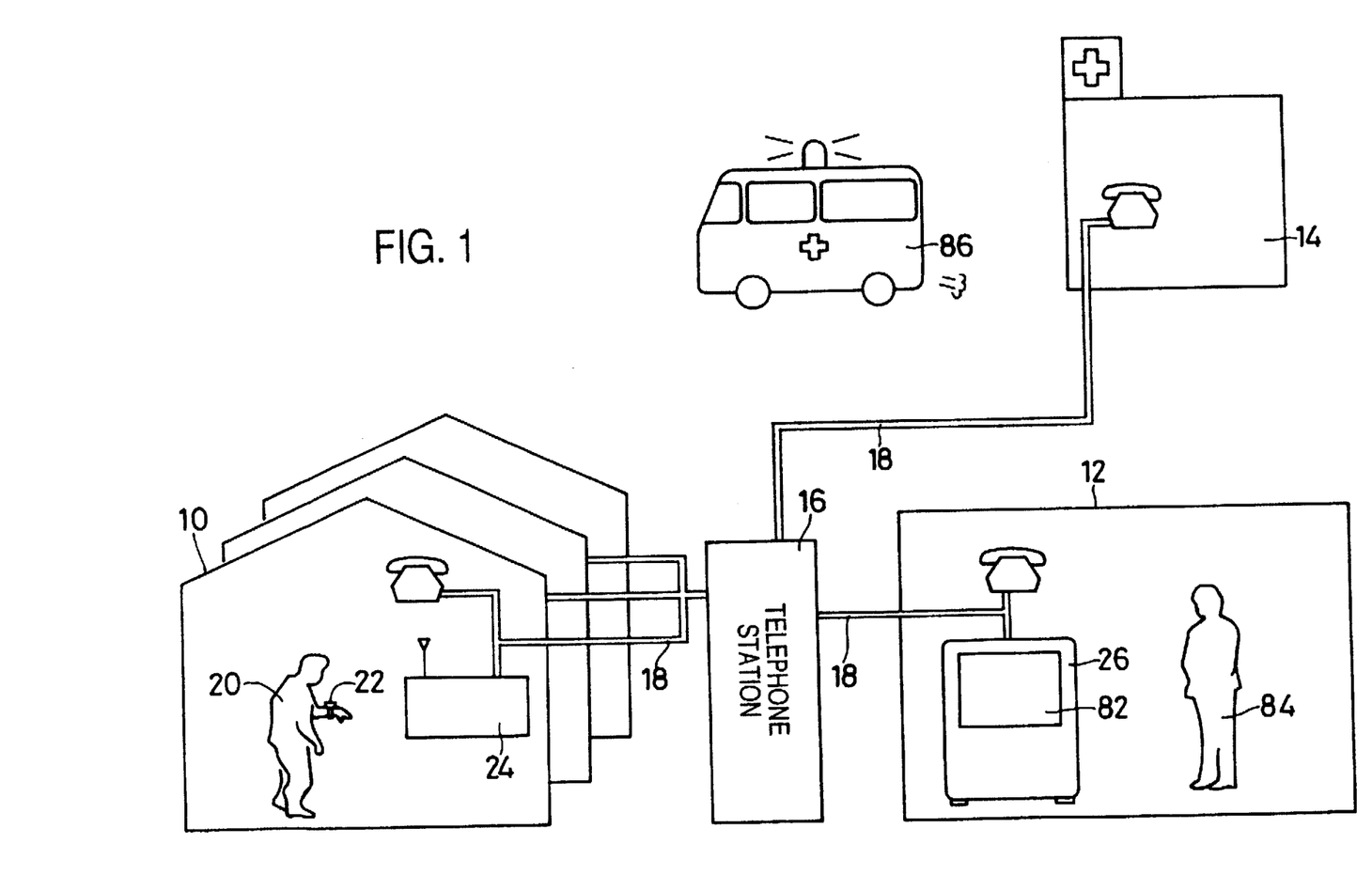
FIG. 1 is an illustrative view of an emergency call system embodying the present invention.

FIG. 1 is an illustrative view of an emergency call system embodying the present invention. In the figure, reference numeral 10 designates a plurality of houses or homes, each of which is connected via a telephone line 18 and a telephone station 16 to an emergency call center 12 and a hospital 14.

In each home 10, there is disposed a portable transmitting device 22 which is adapted to be worn on a subscriber 20. There is also disposed a signal receiving and call device 24 which is connected to the telephone line 18 of a telephone set disposed in the home 10 of the subscriber 20. The emergency call center 12 may be organized in a private emergency service center or a fire department. A host monitor device 26 is disposed in the emergency call center 12 and is connected to the telephone line 18.

Figure 2:
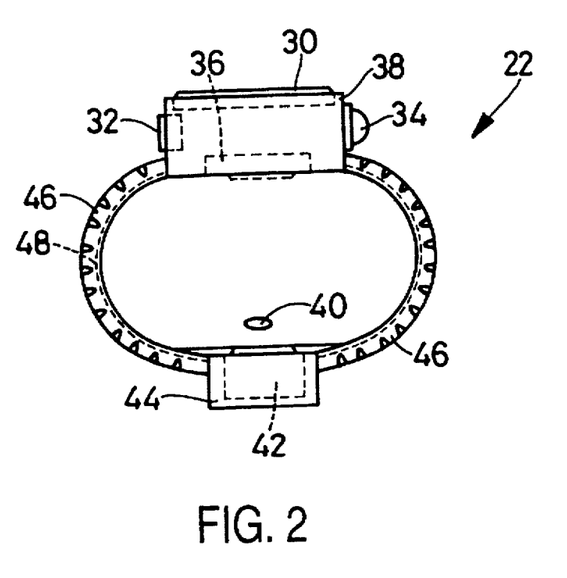
FIG. 2 is a view of a mechanical construction of a portable transmitting device which is adapted to be worn on a subscriber as shown in FIG. 1.

Referring next to FIG. 2, there is shown the portable transmitting device 22 of a watch type. As shown in the figure, the portable transmitting device 22 includes: a first housing 38 comprising a display device 30 which displays pulse wave information such as a pulse rate, a piezoelectric buzzer 32 which issues an alarm sound, a call button 34 which is operable for transmitting an emergency call of the subscriber 20, and a wearing sensor 36; a second housing 44 comprising a pulse wave sensor 42 which detects a pulse wave produced from a radial artery 40 of the subscriber 20 by being pressed on the skin directly above the artery 40; and bands 46 by which the first housing 38 and the second housing 44 are connected to each other and the portable transmitting device 22 is fixed to an arm of the subscriber 20. The bands 46 are formed of, e.g., a synthetic resin which is elastically deformable. An antenna 48 is provided along the bands 46. The pulse wave sensor 42 is a pressure sensor which has the same construction as that of a conventional sensor disclosed in unexamined Japanese Patent Application laid open under Publication No. 3-15440. Namely, the pulse wave sensor 42 detects a pressure pulse wave produced from the radial artery 40 by being pressed on the skin directly above the radial artery 40.

Figure 3:
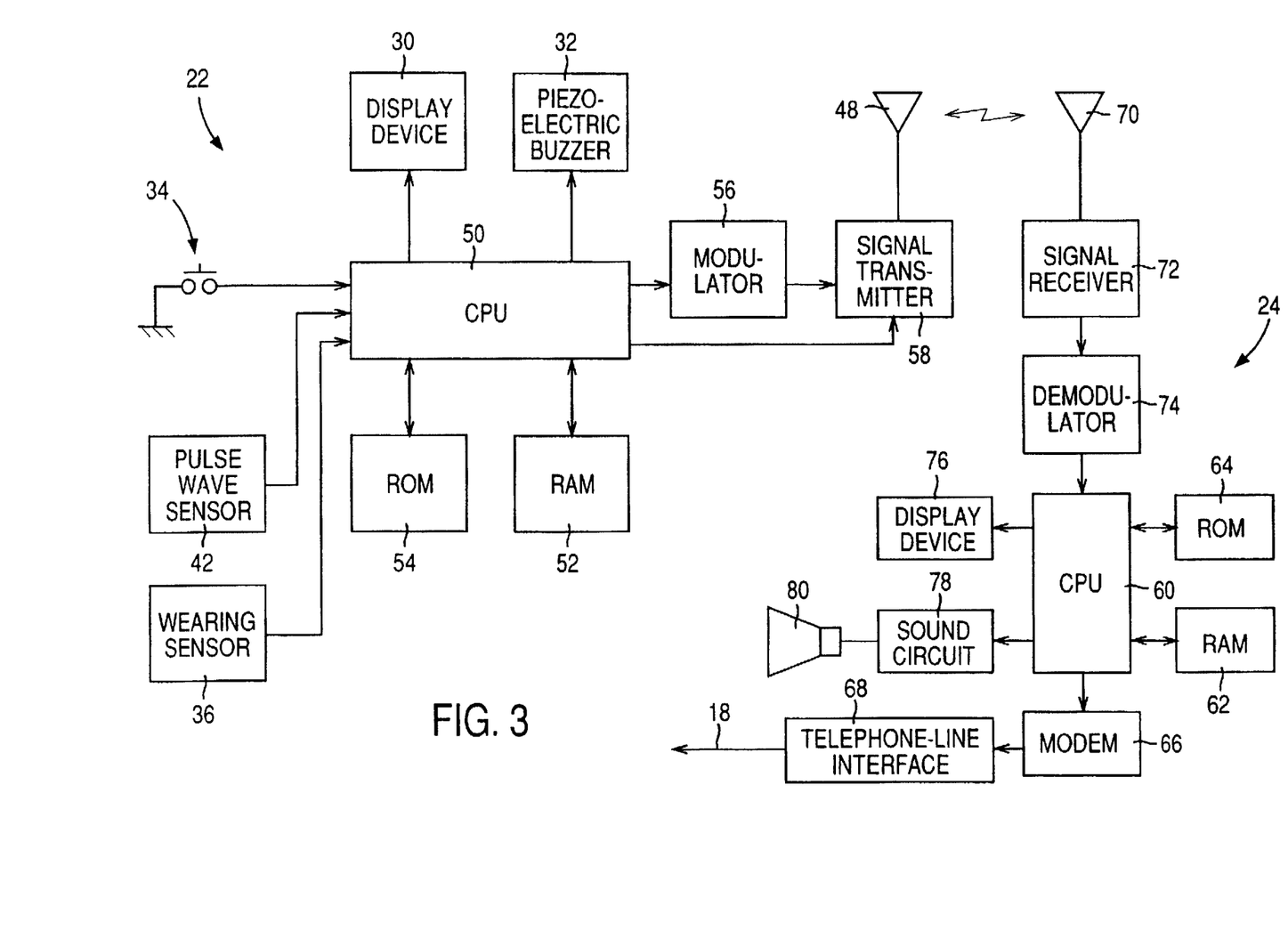
FIG. 3 is a diagrammatic view of respective electric arrangements of the portable transmitting device and a signal receiving and call device shown in FIG. 1.

FIG. 3 shows a diagrammatic view of respective electric arrangements of the portable transmitting device 22 and the signal receiving and call device 24. A central processing unit (CPU) 50 of the portable transmitting device 22 processes input signals according to control programs pre-stored in a read only memory (ROM) 54 by utilizing a temporary-storage function of a random access memory (RAM) 52. An emergency call signal and a pulse rate data signal are transmitted via a modulator 56 and a signal transmitter 58.

Figure 4:
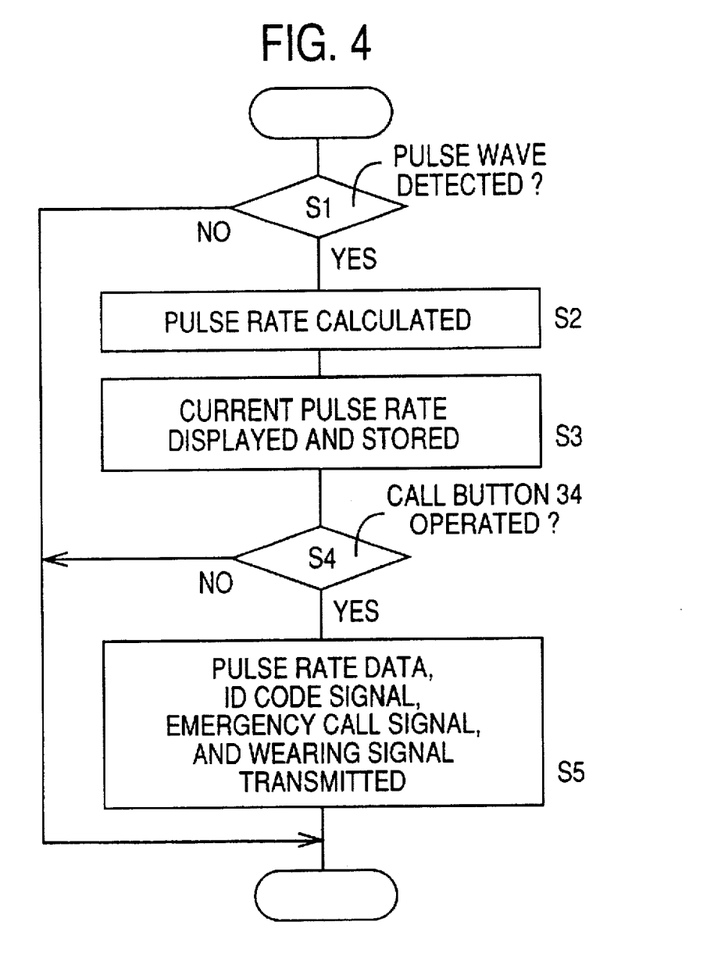
FIG. 4 is a flow chart representing a control program according to which the portable transmitting device of FIG. 3 operates.

FIG. 4 shows a flow chart representing a control program according to which the portable transmitting device 22 operates. First, at Step S1, the CPU 50 judges whether a pulse wave has been detected, based on the input signal from the pulse wave sensor 42. If the pulse wave sensor 42 has not detected any pulse wave, a negative judgement is made at Step S1, so that the current routine is ended. On the other hand, if the pulse wave sensor 42 has detected a pulse wave, a positive judgement is made at Step S1, so that the control goes to Step S2 to calculate a pulse rate based on a time difference between the current pulse wave and the last pulse wave according to a pre-stored expression. At the following Step S3, the CPU operates a display device 30 to display the thus calculated, current pulse rate of the subscriber 20, and stores the current pulse rate in the RAM 52. Step S3 is followed by Step S4 to judge whether the call button 34 has been operated. If the call button 34 has not been pushed, a negative judgement is made at Step S4, so that Steps S1 through S4 are carried out repeatedly. On the other hand, if the call button 34 has been operated, a positive judgement is made at Step S4. Thus, Step S4 is followed by Step S5 at which the CPU 50 transmits the pulse rate data signal representing the pulse rate values that have been determined and stored in the RAM 52 in a prescribed time duration, e.g., one hour, together with an ID code signal identifying the subscriber 20, the emergency call signal, and the wearing signal supplied from the wearing sensor 36, all via the antenna 48. The CPU 50 starts this monitoring operation upon operation of a power switch (not shown). When, the wearing sensor 36 detects during the monitoring operation that the portable transmitting device 22 is not worn on the subscriber 20, the piezoelectric buzzer 32 issues an alarm sound.

A CPU 60 of the signal receiving and call device 24 of FIG. 3, processes input signals according to control programs pre-stored in a ROM 64 by utilizing a temporary-storage function of a RAM 62. The CPU 60 transmits the emergency call signal and an analysis of the pulse rate data to the emergency call center 12 via a modem 66 and a telephone-line interface 68.

Figure 5:
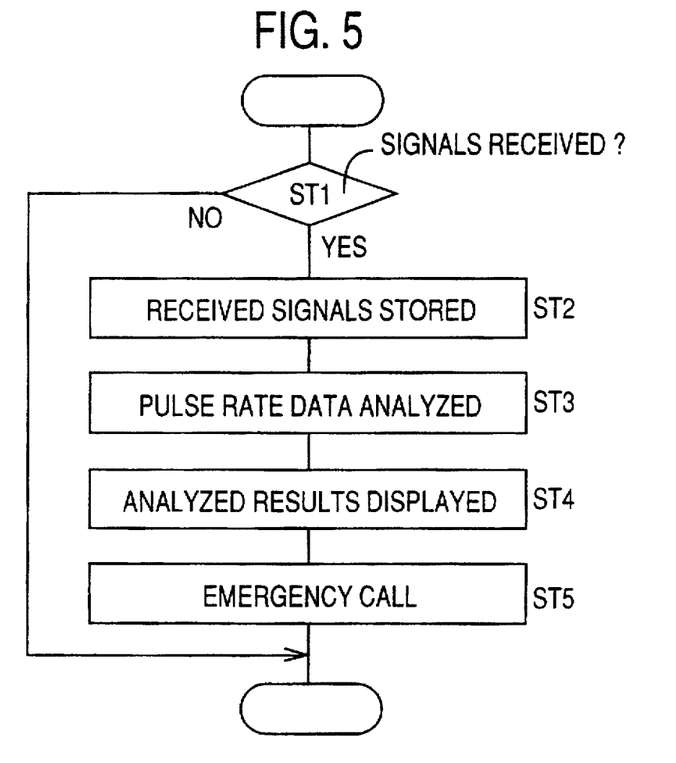
FIG. 5 is a flow chart representing a control program according to which the signal receiving and call device of FIG. 3 operates.

FIG. 5 shows a flow chart representing a control program according to which the signal receiving and call device 24 operates. First, at Step ST1, the CPU 60 judges whether the CPU 60 has received signals from the portable transmitting device 22 via an antenna 70, a signal receiver 72 and a demodulator 74. If the CPU 60 has not received any signals, a negative judgement is made at Step ST1, so that the current routine is ended. On the other hand, if the CPU 60 has received the signals, a positive judgement is made at Step ST1, so that the control of the CPU 60 goes to Step ST2 to store, in the RAM 62, the pulse rate data signal, the ID code signal, the emergency call signal, and the wearing signal. At the following Step ST3, the CPU 60 analyzes the pulse rate data to determine the respective times of day, and total number, of occurrences of arrhythmia, tachycardia and bradycardia of the subscriber 20 in the prescribed time duration. Step ST3 is followed by Step ST4 to operate a display device 76 to display the analyzed results obtained at Step ST3. It is possible that in particular cases a speaker 80 issue a sound or voice by being driven by a sound circuit 78. Step ST4 is followed by Step ST5 to transmit the analysis together with the ID code signal, the emergency call signal, and the wearing signal to the emergency call center 12 via the telephone line 18.

The host monitor device 26 disposed in the emergency call center 12 is supplied with the analysis, the ID code signal identifying the subscriber 20, the emergency call signal and the wearing signal, so that the host monitor device 26 displays on an image display 82 the ID code identifying the subscriber 20, a symbol representing the emergency call, a symbol indicating that the portable transmitting device 22 is worn, or not worn, on the subscriber 20, and the times of day and total number of occurrences of arrhythmia, tachycardia and bradycardia in the last one hour on the subscriber 20. When the operator 84 of the emergency call center 12 receives the emergency call, he or she can check the emergency call against the times of day and total number of occurrences of arrhythmia, tachycardia and bradycardia in the last one hour, i.e., pulse wave information of the subscriber 20 supplied when the call button 34 is operated by the same 20, so that the operator 84 immediately judges whether an emergency action should really be taken in response to the emergency call, without needing an additional checking operation such as a telephone call to the subscriber 20. If the operator 84 judges that an emergency action should be taken, he or she can immediately request a fire department to send an ambulance car to the house 10 of the subscriber 20, and call the hospital 14 at needed.

In the present embodiment, the operator 84 of the emergency call center 12 can recognize that the portable transmitting device 22 is worn on the subscriber 20, based on the symbol representing the wearing signal, together with the ID code identifying the subscriber 20 and the emergency call signal, so that he or she can check the emergency call more accurately. Namely, when the portable transmitting device 22 is not worn on the subscriber 20, the operator 84 can judge that no emergency action is needed, even if the pulse wave information indicates that bradycardia or other abnormal pulse wave has occurred to the subscriber 20.

Next, there will be described another embodiment of the present invention. In the following description, the same reference numerals as used in the preceding, first embodiment are used to designate the corresponding elements of the present, second embodiment of the invention and the explanations of those elements are omitted.

Figure 6:
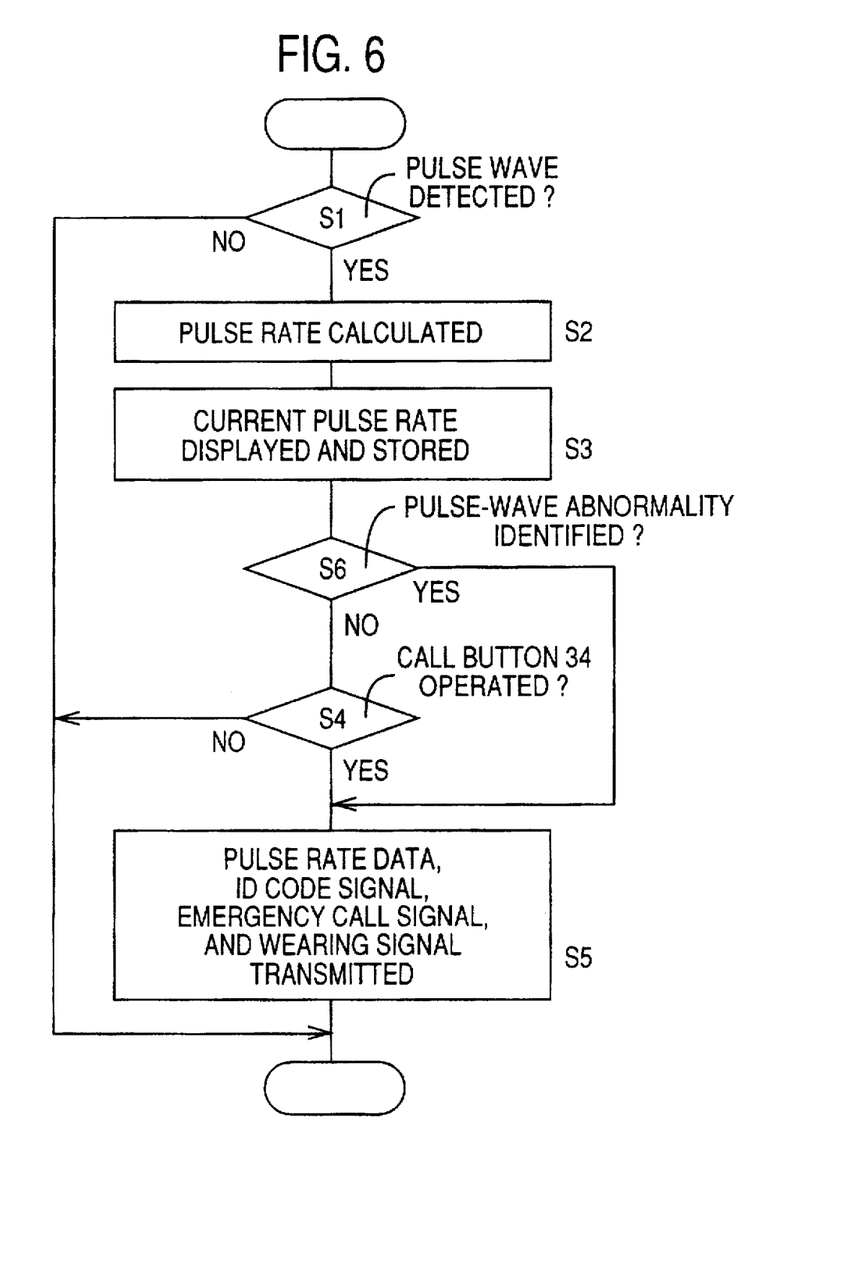
FIG. 6 is a flow chart corresponding to FIG. 4, representing a control program employed in another embodiment of the present invention.

FIG. 6 shows a flow chart representing a modified control program according to which the portable transmitting device 22 operates. The present embodiment is characterized by additionally having Step S6 between Step S3 and Step S4 of the flow chart of FIG. 4 employed in the first embodiment. At Step S6 of FIG. 6, the CPU 60 identifies whether the pulse wave is abnormal, based on the pulse rate calculated at Step S2. Namely, the CPU 60 judges whether the calculated pulse rate value exceeds beyond a standard range of normal pulse rates, or whether the time different between two successive pulses is excessively long. In normal cases, a negative judgement is made at Step S6, the control of the CPU 60 goes to Step S4 and the following steps. On the other hand, if a positive judgement is made at Step S6, the control goes to Step S5 to transmit the pulse rate data obtained in one hour before the identification of abnormality, the ID code signal, the emergency call signal and the wearing signal, to the receiving and call device 24. In the present embodiment, when the CPU 60 identifies that the pulse wave is abnormal at Step S6, the same transmission operation as that carried out in the first embodiment is automatically carried out without subscriber's pushing of the call button 34 needed in the first embodiment.

While the present invention has been described in its embodiments by reference to the accompanying drawings, the present invention may otherwise be embodied.

In the above-described embodiments, the pulse rates are transmitted as the physical information of the subscriber 20. It is otherwise possible to transmit, as the physical information of the subscriber 20, pulse wave information such as a wave form of a pulse wave, a magnitude of a pulse wave, and a blood pressure corresponding to a peak magnitude of a pulse wave. In the later case, the analyzing device of the signal receiving and call device 24 analyzes the respective wave forms of pulse waves, the respective magnitudes of pulse waves, and the blood pressure values.

While in the above-described embodiments the pulse rates obtained through the pulse wave sensor 42 are transmitted as the physical information of the subscriber 20, it is possible to employ, in place of, or in addition to the pulse wave sensor 42, an electrocardiogram sensor, a body temperature sensor, or a sweat sensor. In the later case, electrocardiograms, heart rates, body temperatures, or amounts of sweat, which are obtained through the above-mentioned sensors, may be transmitted to the signal receiving and call device 24 in place of, or in addition to the pulse rates. After all, the portable transmitting device 22 may comprise one or more physical information sensors and may transmit one or more sorts of physical information obtained through the sensor or sensors.

While in the above-described embodiments the signal receiving and call device 24 and the host monitor device 26 are connected to each other via the telephone line 18, the two devices 24, 26 may be connected to each other via a wireless communication channel.

In the above-described embodiments, the pulse wave sensor 42 is a pressure sensor which detects a pressure pulse wave produced from an arterial vessel 40 of a living body. It is otherwise possible to employ a pulse wave sensor which optically detects a pulse wave. In the later case, the portable transmitting device 22 may be worn on body portions of the subscriber 20 other than the arms of the same 20.

Although in the above-described embodiments the respective times of day, and total number, of occurrences of arrhythmia, tachycardia, and bradycardia are transmitted as the analyzed results of the pulse wave information, together with the emergency call signal, to the emergency call center 12, it is otherwise possible to transmit at least one sort of the above-mentioned analyzed results.

While in the above-described embodiments the analyzing device of the signal receiving and call device 24 analyzes the physical information supplied from the portable transmitting device 22, at Step ST 3 of FIG. 5, it is possible to transmit the physical information directly, i.e., without analyzing the information, to the emergency call center 12 via the telephone line 18. Some sorts of physical information may not need any analysis, since those sorts of information, such as pulse rates, may be usable as they are in the form of measured values.

While the present invention has been described in its embodiments, it is to be understood that the present invention may be embodied with other changes and modifications and without departing from the spirit and scope of the invention.

We claim:

1. An emergency call system for transmitting an emergency call of a subscriber to an emergency call center via a communication channel, comprising:

a portable transmitting device having a call button which is operable for transmitting said emergency call of said subscriber, a physical information sensor which obtains a physical information of said subscriber, a memory which stores a batch of physical information detected by said physical information sensor for a predetermined time duration, and a signal transmitter which transmits a signal at a predetermined modulation frequency, said portable transmitting device being adapted to be worn on said subscriber, and transmitting from said signal transmitter an emergency call signal indicative of an operation of said call button and a physical information signal representing said batch of physical information stored in said memory for said predetermined time duration in response to said operation of said call button; and a signal receiving and call device having a signal receiver which receives said emergency call and physical information signals transmitted from said signal transmitter of said portable transmitting device, and a communication apparatus which transmits the emergency call signal and the physical information signal received by said signal receiver to said emergency call center via said communication channel, in response to reception of the signals by the signal receiver, said signal receiving and call device being disposed in a place where said subscriber, said portable transmitting device further comprising a wearing sensor which identifies whether said portable transmitting device is worn on said subscriber and outputs a wearing signal indicating that the portable transmitting device is worn on the subscriber, wherein said signal transmitter transmits said wearing signal and said emergency call and physical information signals in response to said operation of said call button.

2. An emergency call system according to claim 1, wherein said signal receiving and call device transmits said wearing signal and said physical information signal transmitted from said signal transmitter, to said emergency call center.

3. An emergency call system according to claim 1, wherein said portable transmitting device further comprises an abnormality identifying means for identifying whether said subscriber is abnormal, based on said physical information of said subscriber detected by said physical information sensor, wherein said signal transmitter transmits said signal representing said batch of physical information stored in said memory for said predetermined time duration in response to an identification of said abnormality identifying means that said subscriber is abnormal.

4. An emergency call system according to claim 1, wherein said physical information sensor comprises at least one of a pulse wave sensor which detects a pressure pulse wave produced from an arterial vessel of said subscriber, an electrocardiogram sensor which obtains an electrocardiogram from said subscriber, a body temperature sensor which measures a body temperature of said subscriber, and a sweat sensor which measures an amount of sweat perspired from said subscriber.

5. An emergency call system according to claim 4, wherein said batch of physical information comprises at least one of the pressure pulse wave detected by said pulse wave sensor, the electrocardiogram obtained by said electrocardiogram sensor, the body temperature measured by said body temperature sensor, and the amount of sweat measured by said sweat sensor.

6. An emergency call system according to claim 1, wherein said communication channel comprises a telephone line which is connected to a telephone disposed in said place where said subscriber is.

7. An emergency call system for transmitting an emergency call of a subscriber to an emergency call center via a communication channel, comprising:

a portable transmitting device having a call button which is operable for transmitting said emergency call of said subscriber, a physical information sensor which obtains a physical information of said subscriber, a memory which stores a batch of physical information detected by said physical information sensor for a predetermined time duration, and a signal transmitter which transmits a signal at a predetermined modulation frequency, said portable transmitting device being adapted to be worn on said subscriber, and transmitting from said signal transmitter a signal representing said batch of physical information stored in said memory for said predetermined time duration in response to an operation of said call button; and a signal receiving and call device having a signal receiver which receives said signal transmitted from said signal transmitter of said portable transmitting device, an analyzing device which analyzes said signal received by said signal receiver, and a communication apparatus which transmits a signal representing an analysis of said analyzing device to said emergency call center via said communication channel, said signal receiving and call device being disposed in a place where said subscriber is, said portable transmitting device comprising a wearing sensor which identifies whether said portable transmitting device is worn on said subscriber and outputs a wearing signal indicating that the portable transmitting device is worn on the subscriber, wherein said signal transmitter transmits said wearing signal and the physical information signal in response to said operation of said call button, said signal receiving and call device transmitting said wearing signal transmitted from said signal transmitter, and said signal representing said analysis of said analyzing device, to said emergency call center.

8. An emergency call system according to claim 7, wherein said portable transmitting device further comprises an abnormality identifying means for identifying whether said subscriber is abnormal, based on said physical information of said subscriber detected by said physical information sensor, wherein said signal transmitter transmits said signal representing said batch of physical information stored in said memory for said predetermined time duration in response to an identification of said abnormality identifying means that said subscriber is abnormal.

9. An emergency call system according to claim 7, wherein said physical information sensor comprises at least one of a pulse wave sensor which detects a pressure pulse wave produced from an arterial vessel of said subscriber, an electrocardiogram sensor which obtains an electrocardiogram from said subscriber, a body temperature sensor which measures a body temperature of said subscriber, and a sweat sensor which measures an amount of sweat perspired from said subscriber.

10. An emergency call system according to claim 9, wherein said batch of physical information comprises at least one of the pressure pulse wave detected by said pulse wave sensor, the electrocardiogram obtained by said electrocardiogram sensor, the body temperature measured by said body temperature sensor, and the amount of sweat measured by said sweat sensor.

11. An emergency call system according to claim 7, wherein said physical information sensor comprises a pulse wave sensor which detects a pressure pulse wave from said subscriber, wherein said analyzing device analyzes said pressure pulse wave regarding at least one kind of information selected from the group consisting of a pulse rate, a waveform of a pressure pulse wave, a magnitude of a pressure pulse wave, and a blood pressure corresponding to a peak magnitude of a pressure pulse wave.

12. An emergency call system according to claim 7, wherein said communication channel comprises a telephone line which is connected to a telephone disposed in said place where said subscriber is.

13. An emergency call system according to claim 7, wherein said signal receiving and call device further comprises a display device which displays said analysis of said analyzing device so that said subscriber is informed of the analysis.

14. An emergency call system for transmitting an emergency call of a subscriber to an emergency call center via a communication channel, comprising:

a portable transmitting device having a call button which is operable for transmitting said emergency call of said subscriber, a physical information sensor which obtains a physical information of said subscriber, a memory which stores a batch of physical information detected by said physical information sensor for a predetermined time duration, and a signal transmitter which transmits a signal at a predetermined modulation frequency, said portable transmitting device being adapted to be worn on said subscriber, and transmitting from said signal transmitter a signal representing said batch of physical information stored in said memory for said predetermined time duration in response to an operation of said call button; and a signal receiving and call device having a signal receiver which receives said signal from said signal transmitter of said portable transmitting device, and a communication apparatus which transmits the physical information signal received by said signal receiver to said emergency call center via said communication channel, said signal receiving and call device being disposed in a place where said subscriber is, said portable transmitting device further comprising a wearing sensor which identifies whether said portable transmitting device is worn on said subscriber and outputs a wearing signal indicating that the portable transmitting device is worn on the subscriber, wherein said transmitter transmits said wearing signal and said physical information signal in response to said operation of said call button.

15. An emergency call system according to claim 14, wherein said signal receiving and call device transmits said wearing signal, and said physical information signal transmitted from said signal transmitter, to said emergency call center.

* * * * *